US008684924B2

(12) United States Patent
Ouwerkerk et al.

(10) Patent No.: US 8,684,924 B2
(45) Date of Patent: Apr. 1, 2014

(54) DEVICE FOR DETERMINING A STRESS LEVEL OF A PERSON AND PROVIDING FEEDBACK ON THE BASIS OF THE STRESS LEVEL AS DETERMINED

(75) Inventors: Martin Ouwerkerk, Eindhoven (NL); Martijn Krans, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1490 days.

(21) Appl. No.: 11/815,586

(22) PCT Filed: Feb. 3, 2006

(86) PCT No.: PCT/IB2006/050367
§ 371 (c)(1),
(2), (4) Date: Aug. 6, 2007

(87) PCT Pub. No.: WO2006/082565
PCT Pub. Date: Aug. 10, 2006

(65) Prior Publication Data
US 2008/0171914 A1    Jul. 17, 2008

(30) Foreign Application Priority Data
Feb. 7, 2005   (EP) ..................................... 05100832

(51) Int. Cl.
*A61B 5/00*     (2006.01)
*G06F 19/00*    (2011.01)

(52) U.S. Cl.
CPC ..................................... *G06F 19/34* (2013.01)
USPC ........................................................ 600/301

(58) Field of Classification Search
USPC ................................................. 600/300–301
See application file for complete search history.

(56) References Cited

U.S. PATENT DOCUMENTS

| 5,209,494 A | * | 5/1993 | Spector | 273/460 |
| 5,283,735 A | * | 2/1994 | Gross et al. | 600/587 |
| 5,304,112 A | * | 4/1994 | Mrklas et al. | 600/27 |
| 5,993,401 A | * | 11/1999 | Inbe et al. | 601/46 |
| 6,017,360 A | * | 1/2000 | Chubb et al. | 607/88 |
| 6,155,976 A | * | 12/2000 | Sackner et al. | 600/300 |
| 6,350,275 B1 | * | 2/2002 | Vreman et al. | 607/88 |
| 6,493,578 B1 | | 12/2002 | DeFeo | |
| 6,494,850 B1 | | 12/2002 | Kitadou et al. | |
| 6,551,252 B2 | * | 4/2003 | Sackner et al. | 600/536 |
| 6,578,917 B1 | * | 6/2003 | Aubert et al. | 297/317 |

(Continued)

FOREIGN PATENT DOCUMENTS

| GB | 2415051 A | 12/2005 |
| JP | 06000209 A | 1/1994 |
| WO | 2004086968 A1 | 10/2004 |
| WO | 2005032365 A1 | 4/2005 |

*Primary Examiner* — Bill Thomson
*Assistant Examiner* — Bobby Soriano

(57) ABSTRACT

A device (1) for determining a stress related condition of a person and providing feedback about this condition comprises body sensors (20) for detecting stress related body parameters, a stress assessing element (40), and a feedback device, wherein the stress assessing element (40) is designed for processing input provided by the body sensors (20) and for determining control parameters for controlling the feedback device, on the basis of the input provided by the body sensors (20). The body sensors (20) are integrated in a textile structure, so that the tested person does not sense the sensors (20), as a result of which there is no chance that the test results get influenced by an interaction between the device (1) and the person.

16 Claims, 4 Drawing Sheets

(56) References Cited

U.S. PATENT DOCUMENTS

| | | |
|---|---|---|
| 6,807,438 B1 | 10/2004 | Brun Del Re et al. |
| 6,916,274 B2 * | 7/2005 | Glusco .............................. 482/8 |
| 7,672,717 B1 * | 3/2010 | Zikov et al. ................... 600/544 |
| 2002/0045836 A1 * | 4/2002 | Alkawwas .................... 600/509 |
| 2004/0001182 A1 * | 1/2004 | Dyner ............................ 353/28 |
| 2004/0044384 A1 * | 3/2004 | Leber et al. .................... 607/88 |
| 2004/0073079 A1 * | 4/2004 | Altshuler et al. ................. 600/1 |
| 2004/0140988 A1 * | 7/2004 | Kim ............................... 345/700 |
| 2004/0243196 A1 * | 12/2004 | Campos et al. ................. 607/48 |
| 2005/0004631 A1 * | 1/2005 | Benedict ........................ 607/88 |
| 2005/0124851 A1 * | 6/2005 | Patton et al. .................... 600/26 |
| 2005/0264069 A1 * | 12/2005 | Makhsous et al. ......... 297/284.1 |
| 2006/0030907 A1 * | 2/2006 | McNew ......................... 607/88 |
| 2009/0018428 A1 * | 1/2009 | Dias et al. .................... 600/388 |

* cited by examiner

DEVICE FOR DETERMINING A STRESS LEVEL OF A PERSON AND PROVIDING FEEDBACK ON THE BASIS OF THE STRESS LEVEL AS DETERMINED

The present invention relates to a device for determining a stress level of a person and providing feedback on the basis of the stress level as determined, comprising:
at least one body sensor for detecting a stress related body parameter, which is integrated in a textile structure;
a stress assessing element; and
a feedback device;
wherein the stress-assessing element is designed for processing input provided by the body sensor, and for determining control parameters for controlling the feedback device, on the basis of the input provided by the body sensor.

In our fast moving world, more and more people are suffering from emotional stress related musculoskeletal dysfunction, leading to enormous social and financial costs. Hence, there is a great need for devices for detecting emotional stress and for providing appropriate feedback aimed at reducing a stress level of users of the devices.

According to present-day technologies, devices for monitoring stress related patterns of muscle activity are provided. However, these devices require skin-contacted electrodes in order to gather stress status data, so that the actual application of these devices is very annoying to the user. Moreover, the known devices are bound to influence the state of relaxation of the user in a negative way.

An example of a known biofeedback device for facilitating willful stress release is a game called "The Journey to Wild Divine", which teaches breathing techniques to facilitate relaxation and gathers stress data from skin conductance and heart rate variability.

U.S. Pat. No. 5,993,401 discloses a massage chair functioning as a relax inducing device. The massage chair comprises a heart rate detecting unit for detecting heartbeats of a user, a massage applicator of applying a massage stimulus to the user, and a massage control unit including a microcomputer for controlling an action of the massage applicator according to the heartbeat information provided from the detecting unit.

The heart rate detecting unit of the massage chair is provided with a heartbeat sensor and a heartbeat measuring circuit of a microcomputer. For the purpose of smoothly inducing the user into a relax state without a sensation of pressure, it is preferred to use a sensor capable of detecting the heartbeats without being directly loaded to the user. In particular, the heart rate detecting unit is disposed inside a seat cushion of the massage chair.

By continuously monitoring the heart rate of the user and controlling the massage stimulus, the user may be smoothly induced into a relax state, in which the heart rate of the user is at a predetermined level. Furthermore, at any moment, a relax level of the user may be determined on the basis of the level of the heart rate.

It is an objective of the present invention to provide a device for determining a stress level of a person and providing feedback on the basis of the stress level as determined, by means of which it is possible to obtain accurate results, and by means of which it is possible to put a person to a state of complete relaxation, if so desired. This objective is achieved by a device, comprising:
at least one body sensor for detecting a stress related body parameter, which is integrated in a textile structure;
a stress assessing element; and
a feedback device;
wherein the body sensor is designed for measuring electrical signals which are representative of electrical activity inside the body of the person; and
wherein the stress-assessing element is designed for processing input provided by the body sensor, and for determining control parameters for controlling the feedback device, on the basis of the input provided by the body sensor.

In the device according to the present invention, a body sensor for detecting a stress related body parameter is integrated in a textile structure. In this way, it is achieved that the stress level of a person is not influenced by the measurement, which is performed, contrary to a situation in which a sensor, which needs to be put in contact with the person, is applied.

Particularly, the body sensor is adapted to measuring electrical signals, which are representative of electrical activity inside the body of the person. Hence, an outcome of the measurement may be in the form of an electro gram. Depending on the position of the body sensor with respect to the body of the person, the electro gram may provide useful information regarding brain activity, heart activity, and/or muscle activity of the person. For sake of completeness, it is noted that an electro gram providing information in respect of brain activity is often referred to as electroencephalogram (EEG), an electro gram providing information in respect of heart activity is often referred to as electrocardiogram (ECG), and an electro gram providing information in respect of muscle activity is often referred to as electromyogram (EMG).

The information contained by an electro gram is accurate and complete, and any appropriate existing technique may be used for the purpose of interpreting the electro gram. For the purpose of putting a person to a state of complete relaxation, it is an advantageous possibility to measure muscle tensions of the person, and to provide feedback aimed at reducing the muscle tensions to zero. In particular, the muscle tensions are measured when the person is in a state of rest, wherein the muscle tensions are muscle tensions resulting from co-contractions of agonist and antagonist muscles.

It follows from the preceding paragraphs that the device according to the present invention comprises at least one sensor which is capable of measuring electrical signals from the body of a person, while being arranged in a textile structure, i.e. while being invisible and intangible to the person. Due to this, the present invention provides for stress control in a way that is convenient to a user, wherein many possibilities for implementing the invention exist, given the fact that people are almost continuously in contact with textiles such as clothing and upholstery of couches and beds. Unobtrusive integration of muscle tension analyzing technologies into these textiles obviously can lead to unnoticed and pleasant ways to monitor and correct stress indicating muscle behavior. Application of the device according to the present invention may even lead to an enhancement of the state of relaxation of a person, given the fact that contact to a textile may generate a feeling of comfort.

According to the present invention, willful relaxation of human beings is facilitated by integration of at least one component of stress level feedback devices into nearby textiles. The stress level awareness to be created by these biofeedback textiles can be expected to result in a large impact on society by a strong reduction in medical costs related to treatment of stress related physical diseases.

In short, according to the present invention, the stress level of a human being in contact with textiles is measured by measuring electrical signals, which are representative of electrical activity inside the body of the human being, and the stress level is fed back to this human being in order to facilitate willful relaxation by biofeedback.

As a result of the fact that the at least one body sensor of the device according to the present invention is incorporated in a textile structure, it is possible to gather parameters representing the stress level of an examined person in an unobtrusive and pleasant way. It is possible for the stress assessing element and the feedback device of the device to be incorporated in the textile structure as well.

In a practical embodiment of the device according to the present invention, arrays of sensors and other electronic components are embedded into textile environments such as clothing and upholsteries. Distributed capacitive sensors not requiring direct electrical skin contact, e.g. contact less EMG/ECG sensors, are provided for monitoring various stress related parameters (e.g. heart rate variability, muscular co-contraction) of a person in the vicinity of the textile. Multiple motion sensors can be incorporated in the textile as well, to distinguish stress related muscular activities from body movements in dynamic situations. The sensor signals are fed into suitably packaged smart elements containing on-board signal processing algorithms to determine the stress level. Suitable methods of stress level feedback are incorporated (e.g. by light emitting pixels, vibration patches, loudspeakers). Unobtrusive textile integration is achieved by optimizing all electronic components to fit in a textile environment and by interconnecting the components by textile circuitry.

In particular, assessment of the stress level may be performed by determination of heart rate variability and an amount of muscular co-contraction on the basis of an obtained electro gram. The operation of the capacitive sensors is based on capacitive coupling of a conductive patch in the textile with electrical processes in the heart or muscles of the human being.

The feedback device may be operated such as to communicate the calculated stress level to the person. Within the scope of the present invention, many ways of communication are possible. For example, the feedback may be provided by means of color changes in the textile, wherein embedded light emitting diodes (LEDs) may be used. Optionally, multiple sensors are used for more localized detection of the co-contracting muscle actions. Visual feedback on the location of these muscle tension regions can be given by multiple, pixilated, color change areas on the outside of the fabric.

According to another possibility in respect of the feedback device, a piece of furniture for supporting the person is provided, wherein a shape of this piece of furniture is adjustable. For example, the piece of furniture may comprise a chair having a seat portion and a backrest, wherein an angle between the seat portion and the backrest is adjustable. In such a case, feedback is provided by controlling the angle between the seat portion and the backrest of the chair.

Many applications of the device according to the present invention exist. The device according to the present invention may be incorporated in a textile, which is fitted onto the couch of a psychiatrist enabling feedback on the emotional reactions of a patient/client. Further, such a textile may be fitted to the witness chair of a courtroom, to serve as a non-contact lie detector. Ambient intelligence systems may use the stress status data to assess the response to video or audio content of a person sitting in front of a television or listening to an audio system. In this way, relaxing effects of certain types of content may be determined. Also, a textile provided with the device according to the present invention may be used in stress reducing garments, in order to stimulate local muscle relaxation behavior.

The present invention may be applied in many objects, including couches for psychiatrists, witness chairs for courtrooms, living room couches, meeting room chairs, biofeedback clothing, mood sensing carpets, diagnostic chairs for physiotherapists, beds for measuring quality of sleep, and massage chairs.

The present invention also relates to a method for determining a stress level of a person and providing feedback aimed at minimizing this level. According to the present invention, such a method comprises the following steps:

measuring electrical signals, which are representative of electrical activity inside the body of the person, at an extremity of the person, such as a wrist or a forearm, by applying at least one body sensor, which is capable of carrying out the measurement without making direct contact to the body of the person;

analyzing the measured signal in order to find a portion of the signal which is directly related to muscle tensions of the person; and providing feedback in the form of an action aimed at reducing these muscle tensions of the person.

By measuring the muscle tensions of a person and taking appropriate measures for reducing these muscle tensions, it is possible to put the person to a state of complete relaxation. As long as muscle tensions are detected, it is concluded that such a state has not yet been reached.

According to the method, a measurement is performed at an extremity of the person, such as a wrist or a forearm, by applying at least one body sensor. In a practical way of carrying out the method, at least two body sensors are applied, wherein each of the body sensors is positioned such as to perform a measurement at another extremity of the person. For example, in a situation in which measurements are performed at the wrists of the person, an electro gram is obtained, which provides information regarding tensions of the muscles, which are present between the wrists of the person, especially arm and shoulder muscles. In any case, the measurement is not performed near the heart of the person, and the measurement is also not performed near the head (brain) of the person, otherwise it is practically impossible to obtain useful information regarding muscle activity. Instead, only a signal that is mainly determined by heart activity or brain activity is obtained.

The heart activity of a person has a strong influence on the electrical signals of the body of this person. Even if the signals are measured at extremities of the person, the outcome of the measurement is also related to the heart activity. Therefore, in a preferred way of carrying out the method according to the present invention, in order to find the portion of the signal which is directly related to muscle tensions of the person, a portion of the signal that is directly related to heart activity of the person is determined and subtracted from the signal.

The present invention will now be explained in greater detail with reference to the figures, in which similar parts are indicated by the same reference signs, and in which:

FIG. 1 diagrammatically shows components of a device according to the present invention, incorporated in a shirt;

Figure 4:
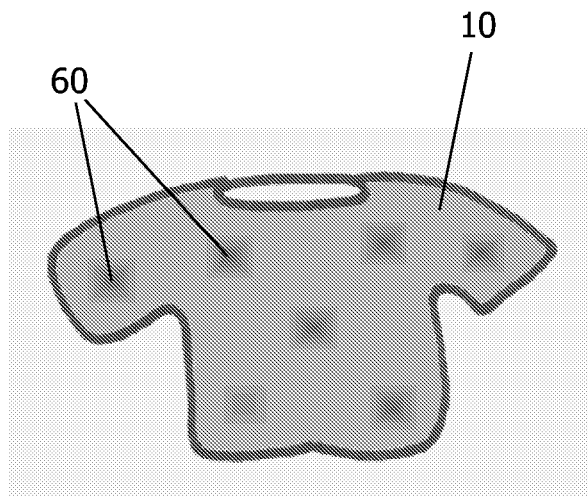
Figure 5:
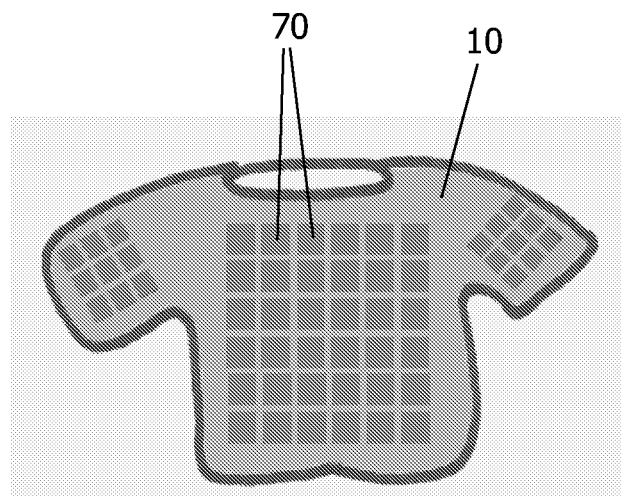
Figure 6:
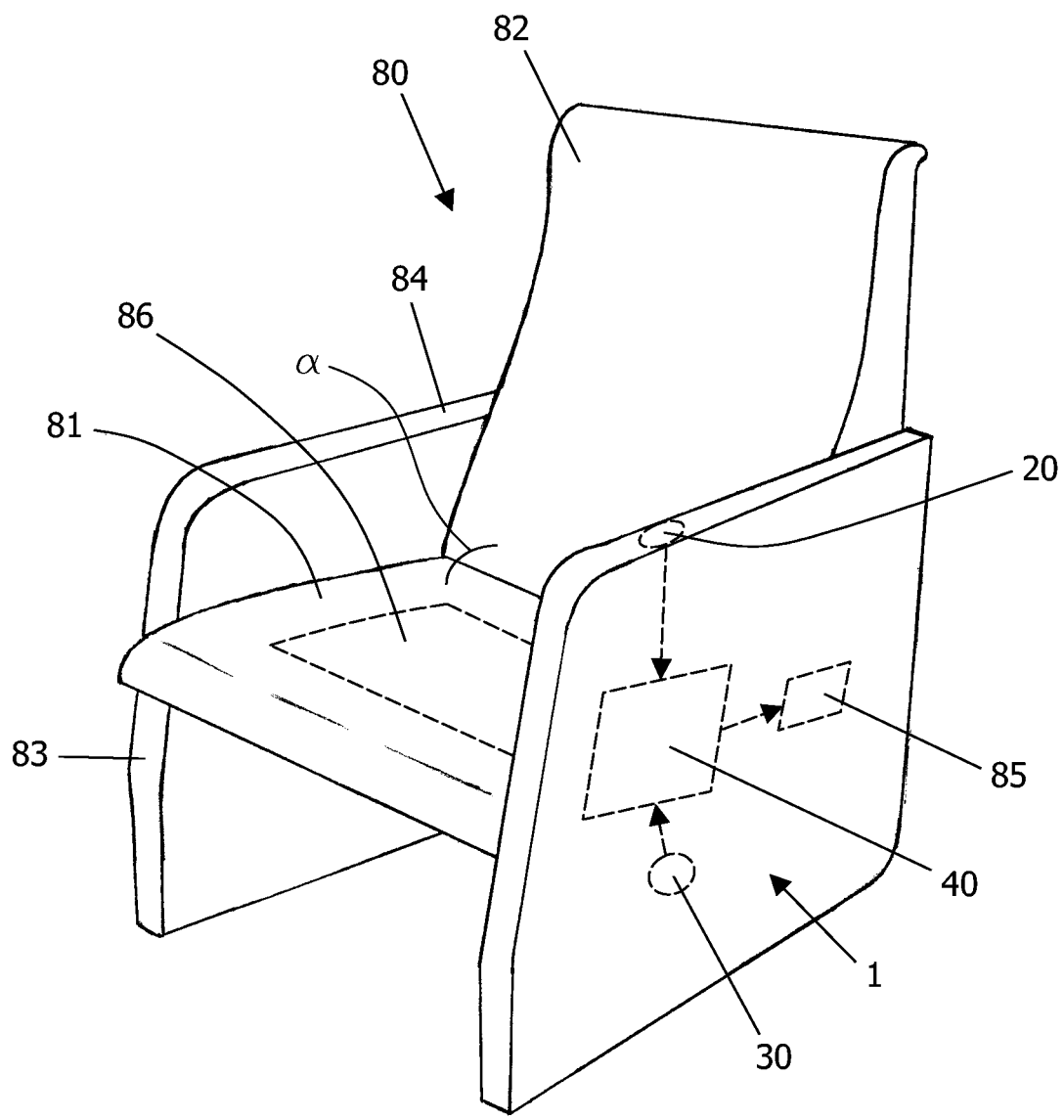
Figure 7:
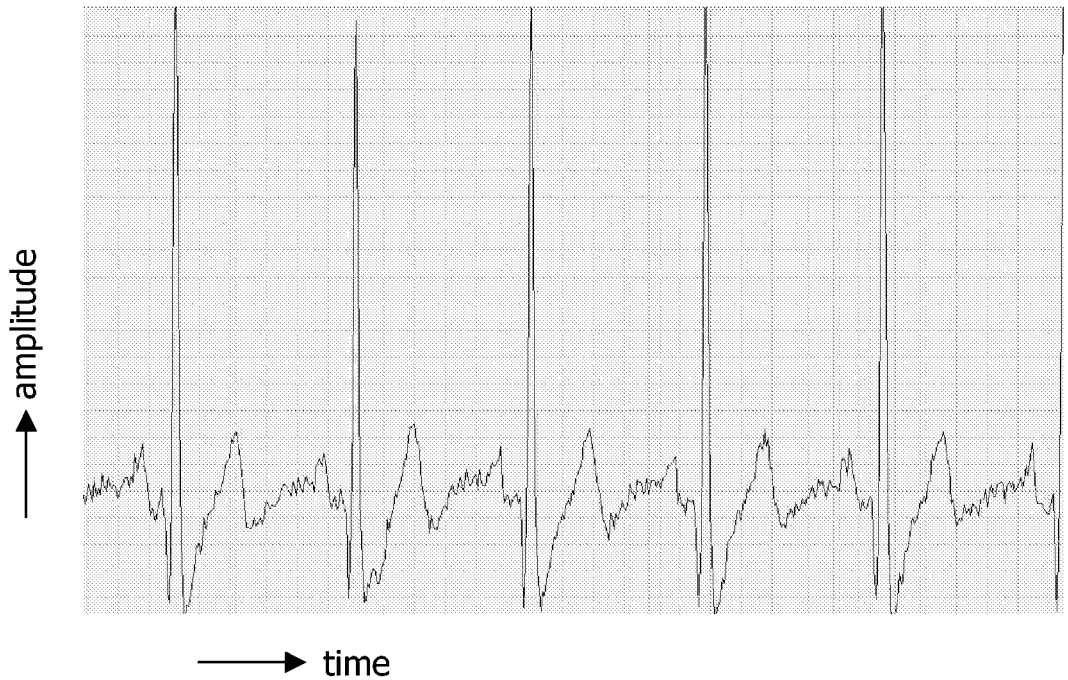
Figure 8:
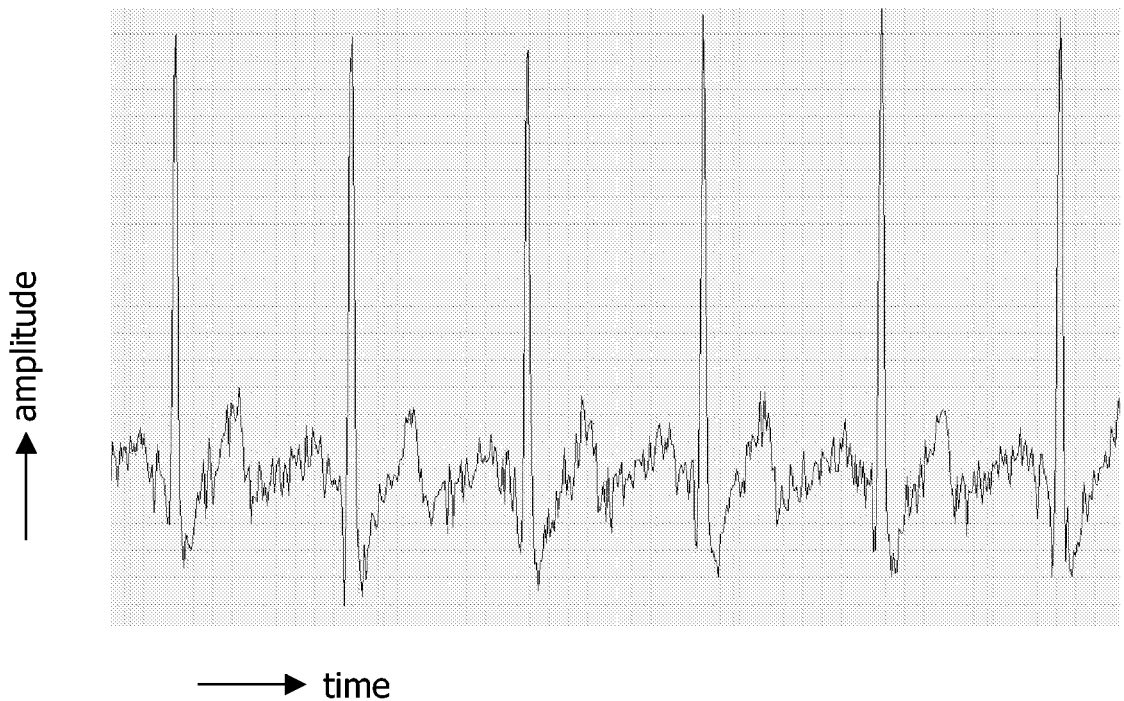

FIG. 4 diagrammatically shows a first possible embodiment of a feedback device, which is part of the device according to the present invention;

FIG. 5 diagrammatically shows a second possible embodiment of a feedback device, which is part of the device according to the present invention;

FIG. 6 diagrammatically shows a chair adapted to putting a person in a state of complete relaxation, comprising components for determining a stress level of the person and for adjusting a shape of the chair;

FIG. 7 shows an electro gram which is obtained by performing measurements at the wrists of a person, wherein the person is in a relaxed state; and FIG. 8 shows an electro gram, which is obtained by performing measurements at the wrists of the same person, wherein the arm and shoulder muscles of the person are tensed.

Figure 1:
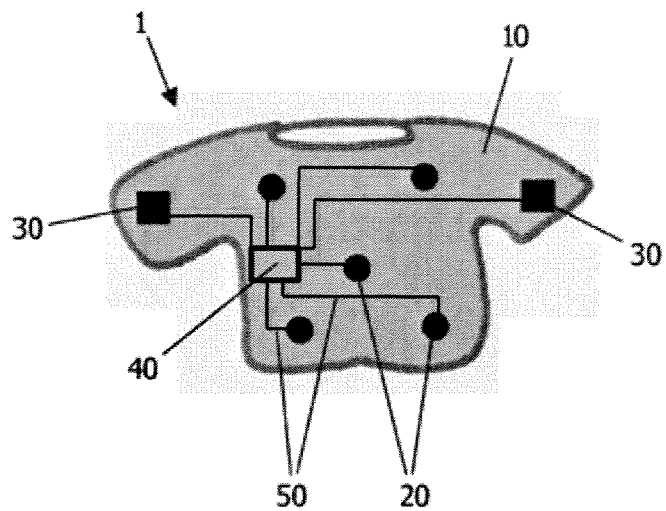

FIG. 1 diagrammatically shows components of a device 1 according to the present invention, incorporated in a shirt 10.

During operation, the device 1 according to the present invention serves as a stress level feedback textile system. The device 1 is capable of fulfilling the following three important tasks:

1) monitoring stress related vital signs of a person in an unperceived way;
2) determining the stress level of the person from these monitored signs; and
3) providing intuitive feedback on vital sign values and the determined stress level.

The device 1 according to the present invention comprises various components, which will be indicated in the following.

For the purpose of detecting stress related body parameters such as muscular co-contraction and heart rate variability, the device 1 according to the present invention comprises body sensors 20. Examples of these sensors are contact less EMG/ECG sensors, body temperature sensors and skin conductance sensors. According to an important aspect of the present invention, the body sensors 20 are integrated in the fabric of the shirt 10, in the form of flexible substrates, capacitive probes or fabric electrodes, for example.

Figure 2:
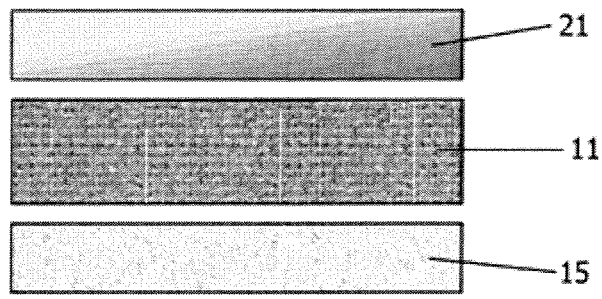
FIG. 2 illustrates the operation of a body sensor, which is part of the device according to the present invention.

FIG. 2 serves for illustrating the operation of a body sensor 20 in the form of a capacitive probe. In particular, the operation of such a body sensor 20 is based on capacitive coupling between electrically conductive patches on the textile and electric processes in the muscles or the heart of the tested person. In FIG. 2, rectangular blocks representing an electrically conductive patch, textile and skin are shown, wherein the electrically conductive patch is indicated by means of reference numeral 21, the textile is indicated by means of reference numeral 11, and the skin is indicated by means of reference numeral 15. During operation of the capacitive sensor 20, the textile 11 serves as a dielectric.

The electrically conductive patches 21 may be applied to the textile in any suitable way, for example by means of attaching electrically conductive flex foils to the textile, or by means of printing electrically conductive ink on the textile. It is also possible that textile patches manufactured from electrically conductive yarns are woven or knitted in a multilayer textile structure, or that these patches are fastened to the textile by means of embroidering or quilting.

For the purpose of detecting parameters relating to the ambiance and a possible motion performed by the tested person in dynamic situations, ambiance and motion sensors 30 are provided. For example, the ambiance and motion sensors 30 may comprise fabric strain/deformation sensors or combined temperature and humidity sensing fibers.

The parameters detected by the ambiance and motion sensors 30 may be used to determine to which extent the body parameters are influenced by ambiance factors and motion of the person. Therefore, on the basis of measuring results from the ambiance and motion sensors 30, it is possible to determine a proper correction of the body parameters detected by the body sensors 20.

Figure 3:
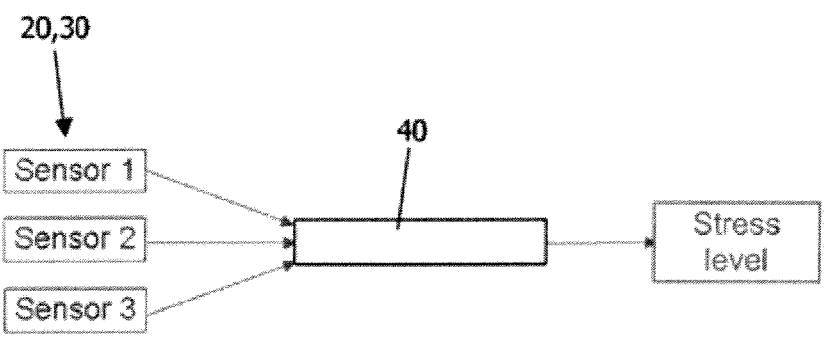
FIG. 3 illustrates the way in which a stress level of a person is determined when the device according to the present invention is applied.

Furthermore, the device 1 according to the present invention comprises a stress-assessing element 40 for processing input supplied by the sensors 20, 30. In a practical embodiment, the stress-assessing element 40 comprises a microprocessor capable of determining the stress level of the tested person by means of signal processing algorithms. The process of the sensors 20, 30 providing input to a signal processor 40, and the signal processor 40 generating output representing the stress level is illustrated by FIG. 3. Examples of technologies applied in the stress-assessing element 40 are the mentioned signal processing algorithms and miniaturized element design.

The sensors 20, 30 and the stress assessing element 40 are interconnected by means of textile interconnects 50. These textile interconnects 50 involve embedding micro-components in textile structures. Examples of suitable technologies are listed below:

Flexible component substrates (flexible foils, ribbons, fabrics)
Encapsulation technologies
Electrical circuitry textile (fabric data and power lines, multilayer weaving concepts, printing circuitry on fabrics)
Micro-to-fabric connections (flexible interposers)
Confection techniques For the purpose of providing feedback about the stress level to the tested person, the device 1 according to the present invention comprises a feedback device. This feedback device may be designed for providing feedback in various ways. Two examples of the way in which feedback may be provided are illustrated by FIGS. 4 and 5.

The feedback device may comprise means for providing intuitive feedback about the stress level of the tested person. This feedback may be provided through visual indicators arranged at an outer side of the fabric, vibrating textile patches (actuators) and/or fabric loudspeakers, for example. Feasible embodiments of visual indicators are light emitting textile structures, e.g. LEDs embedded in fabrics or electro luminescent ink printed on fabric, and color change textile structures, e.g. thermo chrome materials or electro-active materials such as PDLC, E-ink, etc. In FIG. 4, a shirt 10 having LEDs 60 arranged at the outside of the shirt 10 is shown.

Also, the feedback device may comprise means for locally treating/reducing muscle pains when needed. An example of such means is shown in FIG. 5. According to this example, infrared LEDs 70 are arranged at an inner side of a shirt 10. By means of these LEDs 70, the person may be subjected to a so-called low-level light therapy. Apart from the shown infrared LEDs 70, the means for treating the body of the person may also comprise elements for performing a local heat treatment and/or massaging elements, for example.

The device 1 according to the present invention comprises an integrated power supply (not shown) for powering its various components. Such a power supply allows for continuous monitoring. The power supply may comprise thin film, free form lythilene batteries, flexible solar patches or other suitable elements.

In FIG. 6, a perspective view of a chair 80 according to the present invention is shown. Like any commonly known chair, the chair 80 comprises a seat portion 81 and a backrest 82, wherein the seat portion 81 and the backrest 82 are extending at an angle α with respect to each other. In the shown example, the chair 80 comprises two support blocks 83, which are arranged on either side of the seat portion 81 and the backrest 82, and which serve for supporting the seat portion 81 and the backrest 82, among other things. Upper surfaces 84 of the support blocks 83 constitute armrests of the chair 80.

Like any chair, the chair 80 serves for receiving and supporting a person, and has a textile covering. The chair 80 comprises a device 1 capable of determining the stress level of a person sitting on the chair, without making direct contact to the person, and of adapting the mutual position of the seat portion 81 and the backrest 82 in such a way that a most comfortable position is found for this person, wherein the stress level of the person is reduced. In particular, such a position may be a position in which the lower back of the person is supported in the best possible manner. The person may even be put to a state of complete relaxation, in which an amount of muscular co-contraction is practically zero.

The device 1 comprises body sensors 20 which are arranged right underneath the upper surface 84 of each of the support blocks 83, inside the support blocks 83. In FIG. 6, for sake of clarity, only one body sensor 20 is shown, which is diagrammatically depicted by means of a dashed line. The positions of the body sensors 20 are adapted to the most likely position of the wrists and/or the forearms of a person sitting in the chair 80, such that the body sensors 20 may be close to the wrists and/or the forearms. The body sensors 20 are designed for detecting electrical signals, in particular electrical signals that are generated in the body of the person as a result of heart activity and muscular activity.

Besides the body sensors 20, the device 1 also comprises at least one motion sensor 30 such as an accelerometer for detecting movement of the person. When the person exhibits restless behavior, by constantly shifting a leg, for example, this may be detected by the motion sensor 30 and taken into account when determining an appropriate shape of the chair 80. In FIG. 6, a motion sensor 30, which is located inside one of the support blocks 83, is shown, wherein this motion sensor 30 is depicted by means of a dashed line.

The parameters detected by the motion sensors 30 may be used to determine to which extent the parameters as detected by the body sensors 20 are influenced by movements of the person. Therefore, on the basis of measuring results from the motion sensors 30, it is possible to determine a proper correction of the parameters detected by the body sensors 20.

For the purpose of receiving data from the body sensors 20 and the motion sensors 30 and processing these data, the device 1 comprises a stress-assessing element 40. In the shown example, the stress-assessing element 40 is located in one of the support blocks. In FIG. 6, the stress-assessing element 40 is diagrammatically depicted by means of dashed lines.

The stress assessing element 40 is particularly adapted to determining an amount of muscular co-contraction in the body of the person, and to controlling the angle α between the seat portion 81 and the backrest 82 in such a way that the amount of muscular co-contraction is reduced to a level which is as low as possible. For the purpose of adjusting the angle α, the chair 80 comprises an angle setting device 85, which may comprise an electromotor or other suitable driving means for realizing changes in the angle α. During operation of the device 1 for determining the stress level of a person and controlling the angle α for the purpose of putting the person to a state of complete relaxation, the operation of the angle setting device 85 is controlled on the basis of control parameters as determined by the stress assessing element 40.

When a person takes place on the chair 80 and activates the device 1 for obtaining a state of complete relaxation, the body sensors 20 and the motion sensors 30 are activated, and start measuring signals and transmitting output to the stress-assessing element 40. In the stress-assessing element 40, the measuring results are processed, wherein an amount of muscular co-contraction is determined. Also, control parameters for controlling the angle-setting device 85 are determined, on the basis of the requirement of reducing the amount of muscular co-contraction. For example, when the amount of muscular co-contraction appears to be relatively high, control parameters suitable for obtaining an increase of the angle α by means of the angle setting device 85 are determined. Once the new mutual position of the seat portion 81 and the backrest 82 has been realized, the cycle of measuring electrical body signals by means of the body sensors 20, measuring movement of the person by means of the motion sensors 30, processing the measuring results by means of the stress assessing element 40, determining control parameters for controlling the angle setting device 85, and adjusting the angle α by means of the angle setting device 85 is performed all over again, until the measurements reveal that a minimum amount of muscular co-contraction is obtained.

For sake of clarity, in FIG. 6, information flows from the body sensor 20 to the stress assessment element 40, from the motion sensor 30 to the stress assessment element 40, and from the stress assessment element 40 to the angle setting device 85 are diagrammatically depicted by means of dashed arrows.

In FIGS. 7 and 8, as an illustration of an outcome of measurements as performed by the body sensors 20, electro grams are shown. In particular, these electro grams are obtained by performing measurements at the wrists of a person, wherein the electro gram as shown in FIG. 7 is obtained by performing measurements while the person is in a relaxed state, and wherein the electro gram as shown in FIG. 8 is obtained by performing measurements while the muscles of the person are tensed. For sake of completeness, it is noted that an electro gram is a graph of the amplitude of a measured electrical signal (vertical axis) against time (horizontal axis).

The overall appearance of the electro grams is roughly the same, due to the fact that the heart function of the person has been approximately the same in both measurement situations. However, on a more detailed level, differences are distinguishable, which are caused by the fact that the muscular tensions of the person have been different. A comparison of FIG. 7 and FIG. 8 is illustrative of the influence of the muscle tensions on the measured signal.

The electro grams may be regarded as a combination of an electrocardiogram (ECG) and an electromyogram (EMG). On the basis of the EMG, a level of the muscle tensions is determined. The EMG may be obtained by subtracting the ECG from the total electrical signal. For the purpose of determining the ECG, the chair 80 may also be equipped with sensors for performing measurements near the heart.

Within the scope of the present invention, more aspects of the shape of the chair 80 than just the angle α between the seat portion 81 and the backrest 82 may be adjustable. For example, a position of a whole of the seat portion 81 and the backrest 82 may be adjustable with respect to the pair of support blocks 83. Also, the chair 80 may be equipped with a support panel for supporting the lower back of a person, wherein the position of this support panel is adjustable with respect to the backrest 82. Furthermore, the chair 80 may comprise additional components for providing feedback on the basis of a detected stress level. For example, the chair 80 may comprise infrared LEDs, which are incorporated in the backrest 82, and which are activated when the amount of muscular co-contraction is above a predetermined threshold, the chair 80 may comprise a display for providing feedback in a visible form, etc.

Besides the body sensors 20 and the motion sensors 30, the chair 80 may also be equipped with other sensors, for example sensors for detecting a person's presence in the chair 80. Such sensors may be temperature sensors or humidity sensors, for example. Another option in respect of detecting a person's presence in the chair 80 is an application of sensors for determining an extent to which the textile covering of the chair 80 is stretched.

Furthermore, within the scope of the present invention, a chair 80 having a headrest may be provided, wherein at least one body sensor 20 for measuring brain activity is arranged in the headrest. In this way, for example, it is possible to measure a frequency of alpha brainwaves, and to provide feedback aimed at putting this frequency to a predetermined level.

The chair 80 may comprise an integrated power supply (not shown) for powering its various components, but it is also possible that a power circuit of the chair 80 is connectable to the mains by means of a plug, for example.

In a practical application, for the purpose of minimizing the influence of ambiance signals on the measurement of electrical signals following from muscular activity, heart activity and/or brain activity, measures are taken for the purpose of realizing common mode rejection. For example, a sheet of electrically conductive material is incorporated in the seat portion 81. Such a sheet is diagrammatically depicted in FIG. 6 by means of dashed lines, and indicated by means of a reference sign 86. The sheet 86 is coupled to an electrical earth system of the chair 80, while a capacitive coupling between the sheet 86 and the body of the person is established. In order to ensure that a useful effect is obtained by applying the sheet 86, it is preferred if the area of the sheet 86 is large with respect to a total area of the body sensors 20. An alternative to using the electrically conductive sheet 86 is grounding the measuring system on the body of the person.

It will be clear to a person skilled in the art that the scope of the present invention is not limited to the examples discussed in the foregoing, but that several amendments and modifications thereof are possible without deviating from the scope of the present invention as defined in the attached claims.

In the foregoing, a device 1 for determining a stress related condition of a person and providing feedback about this condition is described. Among other components, this device 1 comprises body sensors 20 for detecting stress related body parameters, a stress assessing element 40, and a feedback device 60, 70, 85, wherein the stress assessing element 40 is designed for processing input provided by the body sensors 20 and for determining control parameters for controlling the feedback device 60, 70, 85, on the basis of the input provided by the body sensors 20. The body sensors 20 are integrated in a textile structure, so that the tested person does not sense the sensors 20, as a result of which there is no chance that the test results get influenced by an interaction between the device 1 and the person.

The invention claimed is:

1. A device for determining a stress level of a person and providing feedback on a basis of the stress level as determined, comprising:
   a textile structure;
   at least one body sensor including a patch of electronically conductive textile material integrated in the textile structure, the electrically conductive textile patch measuring electrical signals which are representative of electrical activity inside a body of the person when the textile structure contacts the person's body; and
   a stress assessing device which processes the electrical signals from the at least one body sensor, and determines a stress level of the person and controls parameters for controlling a feedback device in accordance with the determined stress level;
   the feedback device being configured to communicate the stress level to the person;
   wherein the feedback device includes LEDs embedded in the textile structure to change color of at least a portion of the textile structure in accordance with the stress level of the person.

2. The device according to claim 1, further comprising:
   at least one motion sensor which detects movement of the person and provides input to the stress assessing device,
   wherein the stress assessing device processes input provided by both the at least one body sensor and the at least one motion sensor and determines control parameters for controlling the feedback device on the basis of the input provided by both the at least one body sensor and the at least one motion sensor.

3. The device according to claim 1, further including:
   conductive textile connections at least between the electrically conductive textile patch and the stress assessing device.

4. The device according to claim 1, wherein the feedback device provides treatment to the body of the person.

5. The device according to claim 4, wherein the feedback device includes infrared LEDs disposed on an inside of the textile structure to treat at least a portion of the body of the person with infrared light in accordance with the stress level.

6. The device according to claim 1, wherein the textile structure in which the conductive textile patch is integrated is part of a garment.

7. The device according to claim 1, wherein the textile structure in which the at least one conductive textile patch is integrated is part of a piece of furniture.

8. The device according to claim 7, wherein the feedback device adjusts a shape of the piece of furniture in accordance with the determined stress level of the person.

9. A device for determining a stress level of a person and providing feedback on a basis of the stress level as determined, comprising:
   at least one body sensor integrated into a textile structure and configured to detect a stress related body parameter;
   at least one motion sensor configured to detect movement of the person;
   a stress assessing device; and
   a feedback device;
   wherein the stress assessing device is configured to process input provided by both the at least one body sensor and the at least one motion sensor, and configured to determine control parameters for controlling the feedback device, on a basis of the input provided by both the at least one body sensor and the at least one motion sensor; and
   wherein the feedback device is configured to control an angle between a seat portion and a backrest of a piece of furniture, on the basis of the input provided by the at least one body sensor and the at least one motion sensor and includes an infrared light source embedded in the textile structure to treat at least a portion of the body of the person with infrared light in accordance with a stress level.

10. A device for determining a stress level of a person and providing feedback on a basis of the stress level as determined, comprising:
    a piece of furniture having an adjustable shape;

at least one body sensor configured to detect a stress related body parameter and integrated in a textile structure of the piece of furniture;

a stress assessing device which is configured to process input provided by the at least one body sensor, and configured to determine control parameters for controlling the shape of the piece of furniture, on a basis of the input provided by the at least one body sensor; and a feedback device including a light source in the textile structure of the piece of furniture to treat at least a portion of the body of the person with infrared light in accordance with a stress level.

11. The device according to claim 10, wherein the piece of furniture comprises a chair having a seat portion and a backrest wherein an angle between a seat portion and a backrest is adjustable.

12. The device according to claim 10, further comprising at least one motion sensor configured to detect movement of the person and configured to provide input to the stress assessing device, wherein the stress assessing device processes input provided by both the at least one body sensor and the at least one motion sensor and determines control parameters for controlling the shape of the piece of furniture on the basis of the input provided by both the at least one body sensor and the at least one motion sensor.

13. A method for determining a stress level of a person and providing feedback aimed at minimizing the stress level, comprising the steps of;

measuring electrical signals which are representative of electrical activity inside the persons body by applying at least one body sensor which contacts the person's body, the at least one body sensor including a patch of electronically conductive textile material integrated in a textile structure;

analyzing the measured electrical signal in order to find a portion of the signal which is directly related to muscle tensions of the person; and providing feedback in a form of an action aimed at reducing these muscle tensions of the person and a visual signal in accordance with is stress level of the person by LEDs embedded in the textile structure; and providing a piece of furniture including the textile structure having an adjustable shape; and letting the person take place on the piece of furniture;

wherein the action aimed at reducing the muscle tensions of the person involves an adjustment of the shape of the piece of furniture.

14. The method according to claim 13, wherein, in order to find a portion of the signal which is directly related to muscle tensions of the person, a portion of the signal that is directly related to heart activity of the person is determined and subtracted from the signal.

15. The method according to claim 13, wherein the piece of furniture composes a chair, and wherein an adjustment of the shape of the piece of furniture involves an adjustment of an angle between a seat portion and a backrest of the chair.

16. A device for carrying out the method according to claim 13, comprising;

at least one body sensor including a conductive textile patch which measures electrical signals, the conductive textile patch integrated in a textile structure of the piece of furniture and is positioned in a part of the piece of furniture which is configured to support a extremity of the person such that the conductive textile patch measures the electrical signals at the extremity; and a stress assessing device which analyzes the measured electrical signals, and determines control parameters for controlling the shape of the piece of furniture in accordance with the measured electrical signals.

* * * * *